US011198831B2

(12) United States Patent
Barker et al.

(10) Patent No.: US 11,198,831 B2
(45) Date of Patent: Dec. 14, 2021

(54) LUBRICANT FOR A DEVICE

(71) Applicant: KVI LLC, Eden Prairie, MN (US)

(72) Inventors: Alan Thomas Barker, Bloomington, IN (US); Thomas P. Clement, Bloomington, IN (US); Lorena E. Terhune, Switz City, IN (US); Teresa English, Lyons, IN (US)

(73) Assignee: KVI LLC, Eden Prairie, MN (US)

( * ) Notice: Subject to any disclaimer, the term of this patent is extended or adjusted under 35 U.S.C. 154(b) by 35 days.

(21) Appl. No.: 16/263,505

(22) Filed: Jan. 31, 2019

(65) Prior Publication Data

US 2020/0248092 A1 Aug. 6, 2020

(51) Int. Cl.
| | |
|---|---|
| *C10M 129/72* | (2006.01) |
| *C10M 129/16* | (2006.01) |
| *C10M 105/36* | (2006.01) |
| *A61L 31/08* | (2006.01) |
| *A61B 18/00* | (2006.01) |
| *C10N 40/00* | (2006.01) |

(52) U.S. Cl.
CPC ........... *C10M 129/72* (2013.01); *A61L 31/08* (2013.01); *C10M 105/36* (2013.01); *C10M 129/16* (2013.01); *A61B 2018/00142* (2013.01); *A61B 2018/00595* (2013.01); *A61L 2400/10* (2013.01); *C10N 2040/50* (2020.05)

(58) Field of Classification Search
CPC .......... C10M 105/32; C10M 105/36; C10M 105/38; C10M 129/68; C10M 129/74; C10M 2207/28; C10M 2207/283; C10M 2207/2835; C10M 129/72; C10M 129/16; A61L 31/08; A61L 2400/10; C10N 2040/50; A61B 2018/00142; A61B 2018/00595
See application file for complete search history.

(56) References Cited

U.S. PATENT DOCUMENTS

| | | | |
|---|---|---|---|
| 6,150,425 A | 11/2000 | Sekine et al. | |
| 6,193,997 B1 | 2/2001 | Modi | |
| 6,251,425 B1 | 6/2001 | Mathur | |
| 6,254,825 B1 | 7/2001 | Friedman | |
| 6,342,591 B1 | 1/2002 | Zamora et al. | |
| 6,365,171 B1 | 4/2002 | Kennedy et al. | |
| 6,372,755 B2 | 4/2002 | Hanamura et al. | |
| 6,436,367 B1 | 8/2002 | Modi | |
| 6,444,318 B1 | 9/2002 | Guire et al. | |
| 6,455,072 B1 | 9/2002 | Peters et al. | |
| 6,517,869 B1 | 2/2003 | Park et al. | |
| 6,534,070 B1 | 3/2003 | Franke et al. | |
| 6,534,483 B1 | 3/2003 | Bruno et al. | |
| 6,541,018 B1 | 4/2003 | Simonnet et al. | |
| 6,541,649 B2 | 4/2003 | Banerjee et al. | |
| 6,559,183 B1 | 5/2003 | Schmid et al. | |
| 6,562,356 B2 | 5/2003 | Verite et al. | |
| 6,576,679 B2 | 6/2003 | Kimizuka et al. | |
| 6,605,296 B1 | 8/2003 | Stuckler | |
| 6,616,941 B1 | 9/2003 | Seo et al. | |
| 6,638,544 B2 | 10/2003 | Vandana et al. | |
| 6,638,994 B2 | 10/2003 | Crooks et al. | |
| 6,645,522 B2 | 11/2003 | Naeff et al. | |
| 6,660,729 B1 | 12/2003 | Dickason et al. | |
| 6,710,022 B1 | 3/2004 | Kwetkat et al. | |
| 6,723,814 B2 | 4/2004 | Meier et al. | |
| 6,759,052 B1 | 7/2004 | Suzuki et al. | |
| 6,855,328 B2 | 2/2005 | Hei et al. | |
| 6,858,580 B2 | 2/2005 | Ekwuribe et al. | |
| 6,867,182 B2 | 3/2005 | Papadimitriou | |
| 6,878,693 B2 | 4/2005 | Goldshtein | |
| 6,881,726 B2 | 4/2005 | Chang et al. | |
| 6,906,042 B2 | 6/2005 | Mcshane et al. | |
| 6,989,195 B2 | 1/2006 | Anderson | |
| 7,081,450 B2 | 7/2006 | Goldshtein | |
| 7,087,650 B2 | 8/2006 | Lennon | |
| 7,097,849 B2 | 8/2006 | Mishra et al. | |
| 7,129,208 B2 | 10/2006 | Gokel et al. | |
| 7,217,270 B2 | 5/2007 | Clement et al. | |
| 7,217,770 B2 | 5/2007 | Seo et al. | |
| 7,332,527 B2 | 2/2008 | Bronich et al. | |
| 7,358,232 B2 | 4/2008 | Vogt et al. | |
| 7,371,719 B2 | 5/2008 | Stupp et al. | |
| 7,427,410 B2 | 9/2008 | Hubbell et al. | |
| 7,449,180 B2 | 11/2008 | Kisiday et al. | |
| 7,468,394 B1 | 12/2008 | Zhang et al. | |
| 7,491,690 B2 | 2/2009 | Stupp et al. | |

(Continued)

FOREIGN PATENT DOCUMENTS

| | | | |
|---|---|---|---|
| EP | 1534230 B1 * | 12/2009 | ............. A61K 8/342 |
| EP | 1534230 B1 | 12/2009 | |

OTHER PUBLICATIONS

"International Application Serial No. PCT/US2019/066229, International Search Report dated Feb. 25, 2020", 2 pgs.

(Continued)

*Primary Examiner* — Taiwo Oladapo
(74) *Attorney, Agent, or Firm* — Schwegman Lundberg & Woessner, P.A.

(57) ABSTRACT

Various embodiments disclosed relate to a lubricant. The lubricant includes a first non-amphiphilic triglyceride. The lubricant further includes a second non-amphiphilic triglyceride. The second non-amphiphilic triglyceride is different from the first non-amphiphilic triglyceride. The lubricant further includes a non-amphiphilic glycol ester.

19 Claims, No Drawings

(56) References Cited

U.S. PATENT DOCUMENTS

| | | |
|---|---|---|
| 7,534,761 B1 | 5/2009 | Stupp et al. |
| 7,622,277 B2 | 11/2009 | Rehm |
| 7,645,504 B1 | 1/2010 | Pacetti |
| 7,763,663 B2 | 7/2010 | Mccarthy et al. |
| 7,776,348 B2 | 8/2010 | Gardel et al. |
| 7,939,562 B2 | 5/2011 | Grinberg et al. |
| 8,137,699 B2 | 3/2012 | Johnson et al. |
| 8,192,753 B2 | 6/2012 | Essler et al. |
| 8,216,585 B2 | 7/2012 | Weiner et al. |
| 2010/0047296 A1* | 2/2010 | Banowski .............. A61K 8/062 424/401 |
| 2011/0077177 A1* | 3/2011 | Doyen ................ C10M 129/70 508/175 |
| 2014/0165943 A1* | 6/2014 | Dodd .................. C10M 129/54 123/1 A |
| 2014/0251440 A1* | 9/2014 | Morrison ............ C10M 173/00 137/1 |
| 2018/0030351 A1 | 10/2018 | Levy |

OTHER PUBLICATIONS

"International Application Serial No. PCT/US2019/066229, Written Opinion dated Feb. 25, 2020", 5 pgs.

\* cited by examiner

LUBRICANT FOR A DEVICE

BACKGROUND

Lubricants can be used on a wide variety of medical devices to improve performance. Having a suitable lubricant disposed on a device can help to reduce the amount of tissue that builds-up (e.g., clings) on the device during use. However, maintaining effective performance can require constant re-application of lubricant. This can be inconvenient for the user and increase costs of operation as more lubricant is used. Therefore, it may be desirable to develop lubricants that provide effective performance over a longer period of time.

SUMMARY OF THE DISCLOSURE

Various embodiments disclosed relate to a lubricant. The lubricant includes a first non-amphiphilic triglyceride. The lubricant further includes a second non-amphiphilic triglyceride. The second non-amphiphilic triglyceride is different from the first non-amphiphilic triglyceride. The lubricant further includes a non-amphiphilic glycol ester.

Various further embodiments provide a method of making a lubricant. The lubricant includes a first non-amphiphilic triglyceride. The lubricant further includes a second non-amphiphilic triglyceride. The second non-amphiphilic triglyceride is different from the first non-amphiphilic triglyceride. The lubricant further includes a non-amphiphilic glycol ester. The method includes contacting the first non-amphiphilic triglyceride, the second non-amphiphilic triglyceride, and the non-amphiphilic glycol ester.

Various further embodiments provide a kit. The kit includes a container. The container includes a lubricant. The lubricant includes a first non-amphiphilic triglyceride. The lubricant further includes a second non-amphiphilic triglyceride. The second non-amphiphilic triglyceride is different from the first non-amphiphilic triglyceride. The lubricant further includes a non-amphiphilic glycol ester.

Various further embodiments provide a probe. The probe includes tip having a lubricant in contact with at least a portion of the tip. The lubricant includes a first non-amphiphilic triglyceride. The lubricant further includes a second non-amphiphilic triglyceride. The second non-amphiphilic triglyceride is different from the first non-amphiphilic triglyceride. The lubricant further includes a non-amphiphilic glycol ester.

Various further embodiments provide a method of coating a cautery probe. The method includes contacting a tip of the cautery probe with a lubricant. The lubricant includes a first non-amphiphilic triglyceride. The lubricant further includes a second non-amphiphilic triglyceride. The second non-amphiphilic triglyceride is different from the first non-amphiphilic triglyceride. The lubricant further includes a non-amphiphilic glycol ester.

Various further embodiments provide a method of cauterizing tissue. The method includes cauterizing tissue with the probe comprising a tip. The tip has a lubricant at least partially coated thereon. The lubricant includes a first non-amphiphilic triglyceride. The lubricant further includes a second non-amphiphilic triglyceride. The second non-amphiphilic triglyceride is different from the first non-amphiphilic triglyceride. The lubricant further includes a non-amphiphilic glycol ester.

DETAILED DESCRIPTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the disclosure, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%.

The term "organic group" as used herein refers to any carbon-containing functional group. Examples can include an oxygen-containing group such as an alkoxy group, aryloxy group, aralkyloxy group, oxo(carbonyl) group; a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$, OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$, CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R, (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, and C(=NOR)R, wherein R can be hydrogen or a carbon-based moiety; for example, R can be hydrogen, (C$_1$-C$_{100}$)hydrocarbyl, alkyl, acyl, cycloalkyl, aryl, aralkyl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbon atoms or, in some embodiments, from 2 to 8 carbon atoms. Examples include, but are not limited to, vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, alkoxy group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "cycloalkyl" as used herein refers to cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined herein. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups. The term "cycloalkenyl" alone or in combination denotes a cyclic alkenyl group.

The term "aryl" as used herein refers to cyclic aromatic hydrocarbon groups that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, a phenyl group substituted at any one or more of 2-, 3-, 4-, 5-, or 6-positions of the phenyl ring, or a naphthyl group substituted at any one or more of 2- to 8-positions thereof.

The term "aralkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to aromatic and non-aromatic ring compounds containing three or more ring members, of which one or more is a heteroatom such as, but not limited to, N, O, and S.

The term "heteroaryl" as used herein refers to aromatic ring compounds containing 5 or more ring members, of which, one or more is a heteroatom such as, but not limited to, N, O, and S; for instance, heteroaryl rings can have 5 to about 8-12 ring members. A heteroaryl group is a variety of a heterocyclyl group that possesses an aromatic electronic structure.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclyl alkyl groups include, but are not limited to, furan-2-yl methyl, furan-3-yl methyl, pyridine-3-yl methyl, tetrahydrofuran-2-yl ethyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include about 1 to about 12, about 1 to about 20, or about 1 to about 40 carbon atoms bonded to the oxygen atom, and can further include double or triple bonds, and can also include heteroatoms. For example, an allyloxy group or a methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R-NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The terms "halo," "halogen," or "halide" group, as used herein, by themselves or as part of another substituent, mean, unless otherwise stated, a fluorine, chlorine, bromine, or iodine atom.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl $(C_1)$, ethyl $(C_2)$, propyl $(C_3)$, or butyl $(C_4)$, and $(C_0-C_b)$hydrocarbyl means in certain embodiments there is no hydrocarbyl group.

The term "weight-average molecular weight" as used herein refers to $M_w$, which is equal to $\Sigma M_i^2 n_i / \Sigma M_i n_i$, where $n_i$ is the number of molecules of molecular weight $M_i$. In various examples, the weight-average molecular weight can be determined using light scattering, small angle neutron scattering, X-ray scattering, and sedimentation velocity.

The polymers described herein can terminate in any suitable way. In some embodiments, the polymers can terminate with an end group that is independently chosen from a suitable polymerization initiator, —H, —OH, a substituted or unsubstituted $(C_1-C_{22})$hydrocarbyl (e.g., $(C_1-C_{10})$alkyl or $(C_6-C_{20})$aryl) interrupted with 0, 1, 2, or 3 groups independently selected from —O—, substituted or unsubstituted —NH—, and —S—, a poly(substituted or unsubstituted $(C_1-C_{20})$hydrocarbyloxy), and a poly(substituted or unsubstituted $(C_1-C_{20})$hydrocarbylamino).

According to various embodiments, a lubricant can be used in conjunction with many different types of medical devices. The lubricants described herein can be useful in applications where heat is generated by use of the medical device, such as electrosurgery. It has been found that the lubricant described herein, according to various embodiments, can withstand heating over a large amount of cycles (also called burn cycles). It has further been found that the lubricants described herein can help to substantially prevent tissues, e.g., skin, from clinging to the medical device, at locations to which the lubricant is applied. In particular, the lubricant can substantially prevent tissues from clinging to the medical device when the device is used in the first instance. Additionally, according to various embodiments, the color of the lubricant can be controlled to be any suitable color. For example, in a container, the lubricant can have a white or off-white color, after heat is generated, however, the lubricant can be visually transparent. Controlling the color of the lubricant can be helpful in that the color can be selected to look different that a color of a biological fluid. This can help to minimize the risk that the lubricant is mistaken for the biological fluid or vice versa.

According to various embodiments, the lubricant can include a first non-amphiphilic triglyceride; a second non-amphiphilic triglyceride, and a non-amphiphilic glycol ester. According to various embodiments, the first non-amphiphilic triglyceride and the second non-amphiphilic triglyceride differ by of molecular weight, chemical structure, saturation level, isomerization, melting point, polymorph, or a combination thereof. According to various embodiments, a compound can be considered to be non-amphiphilic if the formal charge of substantially every atom of the compound is substantially zero. According to some embodiments, the formal charge of every atom of the compound was zero.

As understood, a triglyceride is a triester of a glycerol and three fatty acids. According to various embodiments, each of the three fatty acids or sub-combinations of the fatty acids can be different. Alternatively, each of the fatty acids can be the same, thus resulting in the triglyceride being a homotriglyceride. A homotriglyceride can be obtained in one of three polymorphs (e.g., α, β, or β') each differing in terms of melting point. Triglycerides can be characterized, in part, by the level of unsaturation or saturation in the structure. Unsaturation is the result of a double bond in the fatty acid chain. Conversely, saturation in the fatty acid chains indicates the absence of a double bond. According to various embodiments, the first non-amphiphilic triglyceride and the second non-amphiphilic triglyceride independently are saturated, mono-unsaturated or poly-unsaturated. For example, the first non-amphiphilic triglyceride can be unsaturated and the second non-amphiphilic triglyceride can be saturated. If the first non-amphiphilic triglyceride or the second non-amphiphilic triglyceride are unsaturated, either triglyceride can be mono-unsaturated or poly-unsaturated.

The first non-amphiphilic triglyceride and the second non-amphiphilic triglyceride can have different weight-average molecular weights. For example, the weight-average molecular weight of the first non-amphiphilic triglyceride can be in a range of from about 500 g/mol to about 1000 g/mol, about 600 g/mol to about 900 g/mol, about 700 g/mol to about 800 g/mol, less than, equal to, or greater than about 500 g/mol, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or about 1000 g/mol. The weight-average molecular weight of the second non-amphiphilic triglyceride can be in a range of from about 800 g/mol to about 1500 g/mol, about 1000 g/mol to about 1200 g/mol, less than, equal to, or greater than about 800 g/mol, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390, 1400, 1410, 1420, 1430, 1440, 1450, 1460, 1470, 1480, 1490, or about 1500 g/mol.

The first and second non-amphiphilic triglycerides can also be characterized by their respective melting points. In order for the lubricant to be a liquid during use, the melting point should be relatively low, but at least below a patient's body temperature. For example, a melting point of the first non-amphiphilic triglyceride and the second non-amphiphilic triglyceride can independently be in a range of from about 3° C. to about 80° C., about 5° C. to about 60° C., less than, equal to, or greater than about 3° C., 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or about 80° C. According to various embodiments, the viscosity and homogeneity of the lubricant is improved when the melting point of the first non-amphiphilic triglyceride and the second non-amphiphilic triglyceride are different. For example, according to various embodiments, a difference between a melting point of the first non-amphiphilic triglyceride and the melting point of the second non-amphiphilic triglyceride can be in a range of from about 10° C. to about 70° C., about 30° C. to about 50° C., less than, equal to, or greater than about 10° C., 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, or about 70° C. According to various further embodiments the viscosity and homogeneity of the lubricant is improved when the melting point of the second non-amphiphilic triglyceride is greater than about 37° C. (e.g., body temperature), greater than about 40° C., greater than about 45° C., or greater than about 50° C. Furthermore the lubricant can be free of any precipitates.

According to various embodiments, the first non-amphiphilic triglyceride and the second non-amphiphilic triglyceride can independently have a structure according to Formula I:

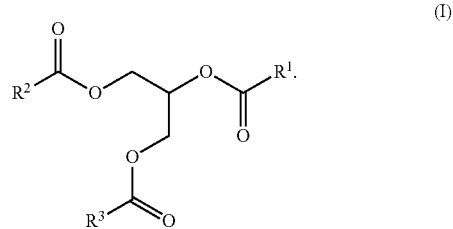

(I)

In Formula I, $R^1$, $R^2$, and $R^3$ can independently be chosen from substituted or unsubstituted ($C_2$-$C_{60}$)hydrocarbyl and a salt thereof. According to various further embodiments, $R^1$, $R^2$, and $R^3$ can independently be chosen from substituted or unsubstituted ($C_2$-$C_{60}$)alkyl, ($C_2$-$C_{60}$)alkenyl, ($C_2$-$C_{60}$)alkynyl, ($C_2$-$C_{60}$)acyl, or a mixture thereof. According to various further embodiments, $R^1$, $R^2$, and $R^3$ can be independently chosen from substituted or unsubstituted ($C_8$-$C_{30}$)alkyl, ($C_8$-$C_{30}$)alkenyl, ($C_8$-$C_{30}$) alkynyl, ($C_8$-$C_{30}$)acyl, or a mixture thereof. According to various further embodiments, $R^1$, $R^2$, and $R^3$ are independently chosen from substituted or unsubstituted ($C_{14}$-$C_{22}$)alkyl or ($C_{14}$-$C_{22}$).

According to various further embodiments, the first non-amphiphilic triglyceride can be triolein, which is derived from glycerol and three units of the unsaturated fatty acid oleic acid. Triolein has the structure according to Formula II:

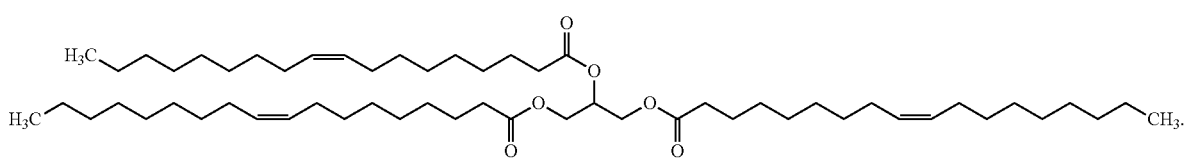

(II)

According to various further embodiments, the second non-amphiphilic triglyceride can be tribehenin, which is derived from glycerol and three units of the saturated fatty acid behenic acid. Tribehenin has the structure according to Formula III:

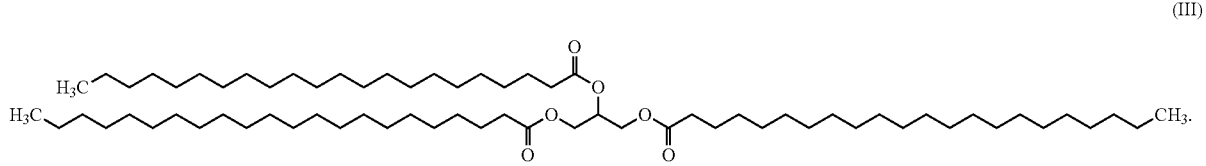 [SMILES: CCCCCCCCCCCCCCCCCCCCCC(=O)OCC(COC(=O)CCCCCCCCCCCCCCCCCCCCC)OC(=O)CCCCCCCCCCCCCCCCCCCCC]

(III)

The first and second non-amphiphilic triglycerides can be present in the lubricant in any suitable concentration (e.g. weight percent, wt %). For example, according to various embodiments, the first non-amphiphilic triglyceride can be a major component of the lubricant and serve as a base oil. In those embodiments, the first non-amphiphilic triglyceride can be in a range of from about 50 wt % to about 95 wt % of the lubricant, about 80 wt % to about 90 wt %, less than, equal to, or greater than about 50 wt %, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or about 95 wt %.

The second non-amphiphilic triglyceride (as well as the non-amphiphilic glycol ester described further herein) can act as a modifier in the lubricant. Specifically, the second non-amphiphilic triglyceride can act as a rheological modifier to control characteristics of the lubricant such as the viscosity and thickness of the lubricant. For example, adding too much of the second non-amphiphilic triglyceride can result in the lubricant being to waxy or flaky for use, whereas adding too little makes the lubricant too runny for use. Additionally, adding to little or too much can result in separation of components or even precipitation of components from solution. According to various embodiments, the second non-amphiphilic triglyceride can be in a range of from about 0.5 wt % to about 20 wt % of the lubricant, about 5 wt % to about 15 wt %, less than, equal to, or greater than about 0.5 wt %, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, or about 20 wt %.

The non-amphiphilic glycol ester of the lubricant can be any compound, or mixture of compounds that is derived from a reaction between a glycol and one or more carboxylic acids. There is great variability the glycols and carboxylic acids that may be reacted. For example the glycol can be an ethylene glycol, propylene glycol, or any other glycol. The glycol ester can also be a polyglycol ester. According to various embodiments, the non-amphiphilic glycol ester can have a symmetric structure. According to various embodiments, non-amphiphilic glycol ester can have the structure according to Formula IV:

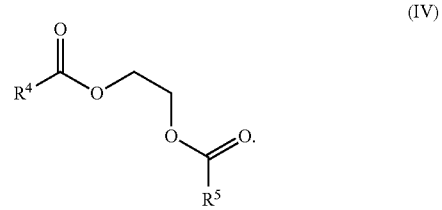

(IV)

In Formula IV, $R^4$ and $R^5$ are independently chosen from substituted or unsubstituted $(C_2-C_{60})$hydrocarbyl or a salt thereof. In further embodiments $R^4$ and $R^5$ can be independently chosen from substituted or unsubstituted $(C_2-C_{60})$alkyl, $(C_2-C_{60})$alkenyl, $(C_2-C_{60})$alkynyl, or a salt thereof. In further embodiments $R^4$ and $R^5$ can be independently chosen from substituted or unsubstituted $(C_8-C_{30})$alkyl, $(C_8-C_{30})$alkenyl, or $(C_8-C_{30})$alkynyl. In further embodiments, $R^4$ and $R^5$ are independently chosen from substituted or unsubstituted $(C_{14}-C_{20})$alkyl or $(C_{14}-C_{20})$. In still further embodiments, the non-amphiphilic glycol ester has the structure according to Formula V:

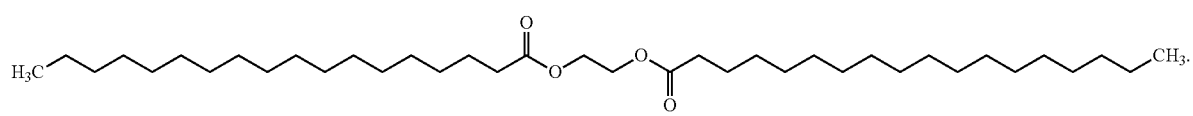

(V)

The non-amphiphilic glycol ester can act as a modifier in the lubricant. Specifically, the non-amphiphilic glycol ester can act as a rheological modifier to control characteristics of the lubricant such as the viscosity and thickness of the lubricant. For example, adding too much of the non-amphiphilic glycol ester can result in the lubricant being to waxy or flaky for use, whereas adding too little makes the lubricant too runny for use. Additionally, adding to little or too much can result in separation of components or even precipitation of components from solution. According to various embodiments, the non-amphiphilic glycol ester can be present in the lubricant in any suitable concentration. For example, the non-amphiphilic glycol ester can be present in a range of from about 2 wt % to about 15 wt % of the lubricant, about 3 wt % to about 6 wt %, less than, equal to, or greater than about 2 wt %, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or about 15 wt % of the lubricant.

The combination of the first and second non-amphiphilic triglycerides, and non-amphiphilic glycol ester can result in the lubricant being substantially homogenous and having any suitable combination of properties. For example, viscosity of the lubricant, measured at about 25° C. can be in a range of from about 5,000 cP to about 15,000 cP, about 8,000 cP to about 12,000 cP, less than equal to, or greater than about, 5,000 cP, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, or about 15,000 cP. Furthermore, the flash point of the lubricant can be tuned to be any desirable value. For example, the flash point of the lubricant is at least about 140° C., at least about 176° C., at least about 200° C., at least about 250° C., in a range of from about 140° C. to about 500° C., about 150° C. to about 200° C., less than, equal to, or greater than about 140° C., 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or about 500° C. The lubricant tends to have an off-white color, but the color can be tuned by adding colorants according to various embodiments.

Although the lubricant is described as including first and second non-amphiphilic triglycerides and a non-amphiphilic glycol ester, it is understood that further embodiments of the lubricant may include additional components. For example, various embodiments of the lubricant may include further non-amphiphilic triglycerides such as a third or fourth non-amphiphilic triglyceride. Still further embodiments of the lubricant may include further non-amphiphilic glycol esters such as a second or third non-amphiphilic glycol ester.

Additional components, that may be included in the lubricant, can include a non-amphiphilic anti-inflammatory component. A non-amphiphilic anti-inflammatory component can be helpful in substantially preventing infections in a patient at sites to which the lubricant is applied. Another potentially suitable additional compound can include a non-amphiphilic fragrance compound. In embodiments, where the lubricant is applied to a cauterization tool, a non-amphiphilic fragrance compound can help to mitigate the unpleasant odor of burning tissue. Another potentially suitable additional component can include a non-amphiphilic anti-oxidant. A non-amphiphilic anti-oxidant component can help to locally mitigate damage caused by oxidation where the lubricant is applied.

According to various embodiments regardless of the amount of or combinations of components present in lubricant, the lubricant is substantially free of amphiphilic compounds. For example, the lubricant can include less than about 0.01 wt % amphiphilic compound, less than about 0.001 wt %, less than about 0.0001 wt %, less than about 0.00001 wt %, or 0 wt % amphiphilic compound. Including an amphiphilic compound can affect the thickness and viscosity of the lubricant. This can lead the poor performance of the lubricant. For example, the lubricant may not be able to withstand a comparable amount of burn cycles, or more tissue may cling to the device to which the lubricant is applied. According to various embodiments, examples of amphiphilic compounds that the compositions can be free of include mono- and di-glycerides, free fatty acids, lecithins (phosphatidylcholine, phosphatidylserine, phosphatidyllysine) both hydrogenated and non-hydrogenated, sterols, waxes (carnauba, beeswax), plant butters (shea, coco, nutmeg), tocopherols, polyglycerol polyricinoleate (PGPR), salts of fatty acids (e.g. Calcium stearate, Magnesium stearate, and the like).

The lubricant described herein can be easily manufactured according to any suitable method. For example, according to various embodiments, a method of manufacturing the lubricant can include contacting the first non-amphiphilic triglyceride, the second non-amphiphilic triglyceride, and the non-amphiphilic glycol ester to form a lubricant precursor. The lubricant precursor can then be heated. The lubricant precursor can be heated to a temperature in a range of from about 70° C. to about 100° C., about 80° C. to about 95° C., less than, equal to, or greater than about 70° C., 71, 72, 73, 74, 75, 76, 77, 78, 79, 80, 81, 82, 83, 84, 85, 86, 87, 88, 89, 90, 91, 92, 93, 94, 95, 96, 97, 98, 99, or about 100° C. During heating, the lubricant precursor can be stirred. Stirring can occur over a range of from about 40 rpm to about 150 rpm, about 60 rpm to about 120 rpm, less than, equal to, or greater than about 40 rpm, 45, 50, 55, 60, 65, 70, 75, 80, 85, 90, 95, 100, 105, 110, 115, 120, 125, 130, 135, 140, 145, or about 150 rpm.

After the lubricant is formed, it can be placed in a container that is adapted to receive, in whole or in part, a probe. The probe can be one of many different types of suitable medical instruments. For example, the probe can be an electro-cautery probe, a scalpel, a heated scalpel, an ultrasonic cutting device, or a radio frequency probe. The probe can include a tip to which the lubricant is at least partially applied. The tip can be adapted to cut and cauterize a tissue. The material of the tip can be any suitable material such as a metal, a ceramic, a composite, a plastic or a mixture thereof. Examples of suitable metals include stainless steel such as SAE 304 stainless steel, SAE 316 stainless steel, and a mixture thereof. In some embodiments, the tip may be coated with a polymer such as a fluoro-polymer (e.g., polytetrfluoroethylene).

The lubricant is able to adhere to the tip. The lubricant may not be permanently adhered to the tip, but the adherence can be sufficient to allow the tip to be transferred from the container to the tissue. In operation, the lubricant can remain on the tip in a substantially liquid form. However, in some embodiments, during use a film is formed on the tip. The film is a polymerized product of the first non-amphiphilic triglyceride and the second non-amphiphilic triglyceride. The film can at least partially coat the tip and can coexist with the lubricant in the liquid phase. According to various embodiments, the film can provide lubricating properties.

The probe can be used for many different purposes. For example, the probe can be used to cauterize, desiccate, cut, or ablate tissue. The probe may be used by a surgeon or robot. If the probe is used to cauterize tissue, an undesirable outcome is that tissue can stick or cling to the probe after each round of cauterization. Applying a lubricant to the tip can help to mitigate this as the tissue will be less likely to stick to the probe. The instantly described lubricant mitigates this by making it more difficult for tissue to adhere to the tip, but by also lasting through many heating cycles while substantially preventing the buildup of tissue thereon.

EXAMPLES

Various embodiments of the present disclosure can be better understood by reference to the following Examples which are offered by way of illustration. The present disclosure is not limited to the Examples given herein.

Example 1: Formulations

Various formulations of a lubricant were developed and tested for their performance. For each formulation the amount and concentration of each formulation is listed along with qualitative notes about the performance of each formulation with respect to its performance as a lubricant.

TABLE 1

| Formula 1 | | |
| --- | --- | --- |
| Compound | Grams | wt % |
| triolein | 5 | 83.33 |
| tribehenate | 0.75 | 12.50 |
| glycol distearate | 0.25 | 4.16 |

Formula 1 performed acceptably as a lubricant.

TABLE 2

| Comparative Formula 1 | | |
| --- | --- | --- |
| Compound | Grams | wt % |
| heptanoin | 4 | 80.81 |
| trimyristin | 0.5 | 10.10 |
| stearin | 0.25 | 5.05 |
| glycol distearate | 0.2 | 4.04 |

Comparative Formula 1 performed unacceptably as a lubricant. The texture of the formula was too waxy and crumbled.

TABLE 3

| Comparative Formula 2 | | |
| --- | --- | --- |
| Compound | Grams | wt % |
| heptanoin | 4 | 80.00 |
| pentaerythritol tetrastearate | 0.5 | 10.00 |
| stearin | 0.5 | 10.00 |

Comparative Formula 2 performed unacceptably as a lubricant. The texture of the formula was too thick and crumbled.

TABLE 4

| Comparative Formula 3 | | |
| --- | --- | --- |
| Compound | Grams | wt % |
| triolein | 4.5 | 92.78 |
| carnauba wax | 0.35 | 7.22 |

Comparative Formula 3 performed unacceptably as a lubricant. The formula separated into phases.

TABLE 5

| Comparative Formula 4 | | |
| --- | --- | --- |
| Compound | Grams | wt % |
| triolein | 4 | 89.00 |
| glycol distearate | 0.5 | 11.00 |

Comparative Formula 4 performed unacceptably as a lubricant. The formula was too thin and was very runny.

TABLE 6

| Comparative Formula 5 | | |
| --- | --- | --- |
| Compound | Grams | wt % |
| triolein | 4 | 87.91 |
| trimyristin | 0.3 | 6.59 |
| stearin | 0.25 | 5.49 |

Comparative Formula 5 performed unacceptably as a lubricant. Too much tissue clung to a cauterization probe during use.

TABLE 7

| Comparative Formula 6 | | |
| --- | --- | --- |
| Compound | Grams | wt % |
| triolein | 5 | 91.00 |
| tribehenate | 0.5 | 9.00 |

Comparative Formula 6 performed unacceptably as a lubricant. Too much tissue clung to a cauterization probe during use and the formula was too thin.

TABLE 8

| Comparative Formula 7 | | |
| --- | --- | --- |
| Compound | Grams | wt % |
| triolein | 5 | 87.00 |
| tribehenate | 0.75 | 13.00 |

Comparative Formula 7 performed unacceptably as a lubricant. There was too much separation between the compounds in solution.

TABLE 9

| Comparative Formula 8 | | |
| --- | --- | --- |
| Compound | Grams | wt % |
| triolein | 4 | 90.00 |
| stearin | 0.3 | 6.74 |
| glycol distearate | 0.15 | 3.26 |

Comparative Formula 8 performed unacceptably as a lubricant. There was too much separation between the compounds in solution and the formula was too thin.

TABLE 10

| Comparative Formula 9 | | |
| --- | --- | --- |
| Compound | Grams | wt % |
| triolein | 4 | 86.96 |
| stearin | 0.4 | 8.70 |
| glycol distearate | 0.2 | 4.35 |

Comparative Formula 9 performed unacceptably as a lubricant. Too much tissue clung to a cauterization probe during use and the formula was too thin.

TABLE 11

| Comparative Formula 10 | | |
| --- | --- | --- |
| Compound | Grams | wt % |
| triolein | 4 | 90.00 |
| stearin | 0.32 | 7.24 |
| glycol distearate | 0.1 | 2.76 |

Comparative Formula 10 performed unacceptably as a lubricant. Too much tissue clung to a cauterization probe during use.

TABLE 12

| Comparative Formula 11 | | |
| --- | --- | --- |
| Compound | Grams | wt % |
| triolein | 4 | 88.89 |
| stearin | 0.5 | 11.11 |

Comparative Formula 11 performed unacceptably as a lubricant. Too much tissue clung to a cauterization probe during use the texture of the formulation was also grainy.

TABLE 13

| Comparative Formula 12 | | |
| --- | --- | --- |
| Compound | Grams | wt % |
| fractionated coconut oil | 4 | 93.02 |
| stearin | 0.3 | 6.98 |

Comparative Formula 12 performed unacceptably as a lubricant. The stearin precipitated out of solution.

TABLE 14

| Comparative Formula 13 | | |
| --- | --- | --- |
| Compound | Grams | wt % |
| fractionated coconut oil | 4 | 88.89 |
| trimyristin | 0.5 | 11.11 |

Comparative Formula 13 performed unacceptably as a lubricant. The trimyristin precipitated out of solution.

TABLE 15

| Comparative Formula 14 | | |
| --- | --- | --- |
| Compound | Grams | wt % |
| triolein | 4 | 80.00 |
| trilaurin | 0.3 | 6.00 |
| stearin | 0.5 | 10.00 |
| glycol distearate | 0.2 | 4.00 |

Comparative Formula 14 performed unacceptably as a lubricant. The texture of the formulation was too grainy.

TABLE 16

| Comparative Formula 15 | | |
| --- | --- | --- |
| Compound | Grams | wt % |
| triolein | 2.5 | 79.11 |
| tricaprin | 0.23 | 7.28 |
| trilaurin | 0.23 | 7.28 |
| glycol distearate | 0.2 | 6.33 |

Comparative Formula 15 performed unacceptably as a lubricant. The texture of the formulation was too grainy.

TABLE 17

| Comparative Formula 16 | | |
| --- | --- | --- |
| Compound | Grams | wt % |
| triolein | 5 | 84.75 |
| tribehenate | 0.5 | 8.47 |
| stearin | 0.2 | 3.39 |
| glycol distearate | 0.2 | 3.39 |

Comparative Formula 16 performed unacceptably as a lubricant. There was too much separation between the components.

TABLE 18

| Comparative Formula 17 | | |
| --- | --- | --- |
| Compound | Grams | wt % |
| C8:C12 MCT Oil | 5 | 87.72 |
| stearin | 0.5 | 8.77 |
| glycol distearate | 0.2 | 3.51 |

Comparative Formula 17 performed unacceptably as a lubricant. Solids precipitated out of solution.

TABLE 19

| Comparative Formula 18 | | |
| --- | --- | --- |
| Compound | Grams | wt % |
| C8:C12 MCT Oil | 5 | 84.03 |
| stearin | 0.75 | 12.61 |
| glycol distearate | 0.2 | 3.36 |

Comparative Formula 18 performed unacceptably as a lubricant. Solids precipitated out of solution.

TABLE 20

| Comparative Formula 19 | | |
|---|---|---|
| Compound | Grams | wt % |
| C8:C12 MCT Oil | 2 | 33.61 |
| triolein | 3 | 50.42 |
| stearin | 0.75 | 12.61 |
| glycol distearate | 0.2 | 3.36 |

Comparative Formula 19 performed unacceptably as a lubricant. The formula was too thin to be used.

TABLE 21

| Comparative Formula 20 | | |
|---|---|---|
| Compound | Grams | wt % |
| C8:C12 MCT Oil | 0.5 | 8.33 |
| stearin | 0.75 | 12.50 |
| glycol distearate | 0.25 | 4.17 |
| C8:C12 MCT Oil | 0.5 | 8.33 |

Comparative Formula 20 performed unacceptably as a lubricant. The formula had a thick and waxy texture.

TABLE 22

| Comparative Formula 21 | | |
|---|---|---|
| Compound | Grams | wt % |
| C8:C12 MCT Oil | 4 | 90.91 |
| tricaprin | 0.4 | 9.09 |

Comparative Formula 21 performed unacceptably as a lubricant. The formula was too thin.

TABLE 23

| Comparative Formula 22 | | |
|---|---|---|
| Compound | Grams | wt % |
| C8:C12 MCT Oil | 2 | 80.00 |
| tricaprin | 0.2 | 8.00 |
| trilaurin | 0.3 | 12.00 |

Comparative Formula 22 performed unacceptably as a lubricant. Solids precipitated out of solution.

Example 2: Burn Cycle Testing

Two lubricants were tested to determine the amount of burn cycles they could endure when deployed on a cauterization tool. The first lubricant had a formulation corresponding to the that of Formula 1 from Example 1. The second lubricant, Comparative Formula 23 was an amphiphilic soy lecithin available under the trade designation ALCOLEC, S GRADE, available from American Lecithin Company, Oxford Conn., USA.

About 100 mg of Formula 1 and Comparative Formula 23, were applied to the tip of a cauterization probe, respectively. The tip included a stainless steel material. The tip of the probe was inserted into a chicken breast and activated for 5 seconds. The probe was then deactivated for 2 seconds before being removed. This constituted one burn cycle. Following removal, the tip was inspected if any chicken breast material remained on the tip, then it was determined that tissue cling occurred. If the tip was free of chicken breast material, then the probe was moved to an adjacent location on the chicken breast and another burn cycle was performed. All tests were conducted at about 25° C. on chicken that was also at about 25° C. and kept moist for consistency in probe performance. The cauterization generator connected to the probe was a model #: MF 360 B available from Aspen Labs, Inc., The generator was set to monopolar coagulation mode at full power.

Formula 1 was tested across 34 trials for a total of 566 burn cycles. The mean value of the number of burns before tissue cling occurred was 16.65 burns/trial. The standard error of the mean was +/−0.87. A total of 100 mg of Formula was consumed per trial.

Comparative Formula 23 was tested across 28 trials for a total of 234 burn cycles. The mean value of the number of burns before tissue cling occurred was 8.36 burns/trial. The standard error of the mean was +/−0.63. A total of 100 mg of Comparative Formula 23 was consumed per trial.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present disclosure. Thus, it should be understood that although the present disclosure has been specifically disclosed by specific embodiments and optional features, modification and variation of the concepts herein disclosed may be resorted to by those of ordinary skill in the art, and that such modifications and variations are considered to be within the scope of embodiments of the present disclosure.

ADDITIONAL EMBODIMENTS

The following exemplary embodiments are provided, the numbering of which is not to be construed as designating levels of importance:

Embodiment 1 provides a lubricant comprising:
a first non-amphiphilic triglyceride;
a second non-amphiphilic triglyceride, different from the first non-amphiphilic triglyceride; and
a non-amphiphilic glycol ester.

Embodiment 2 provides the lubricant of Embodiment 1, wherein the first non-amphiphilic triglyceride and the second non-amphiphilic triglyceride differ by of molecular weight, chemical structure, saturation level, isomerization, melting point, polymorph, or a combination thereof.

Embodiment 3 provides the lubricant of any one of Embodiments 1 or 2, wherein the first non-amphiphilic triglyceride the second amphiphilic triglyceride, or both, are homotriglycerides.

Embodiment 4 provides the lubricant of any one of Embodiments 1-3, wherein the first non-amphiphilic triglyceride and the second non-amphiphilic triglyceride independently have a structure according to Formula I:

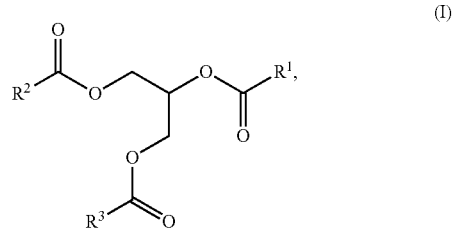

wherein R¹, R², and R³ are independently chosen from substituted or unsubstituted $C_2$-$C_{60}$)hydrocarbyl and a salt thereof.

Embodiment 5 provides the lubricant of Embodiment 4, wherein R¹, R², and R³ are independently chosen from substituted or unsubstituted ($C_2$-$C_{60}$)alkyl, ($C_2$-$C_{60}$)alkenyl, ($C_2$-$C_{60}$)alkynyl, ($C_2$-$C_{60}$)acyl, or a mixture thereof.

Embodiment 6 provides the lubricant of any one of Embodiments 4 or 5, wherein R¹, R², and R³ are independently chosen from substituted or unsubstituted ($C_8$-$C_{30}$) alkyl, ($C_8$-$C_{30}$)alkenyl, ($C_8$-$C_{30}$) alkynyl, ($C_8$-$C_{30}$)acyl, or a mixture thereof.

Embodiment 7 provides the lubricant of any one of Embodiments 4-6, wherein R¹, R², and R³ are independently chosen from substituted or unsubstituted ($C_{14}$-$C_{22}$)alkyl or ($C_{14}$-$C_{22}$).

Embodiment 8 provides the lubricant of any one of Embodiments 4-7, wherein the first non-amphiphilic triglyceride has the structure according to Formula II:

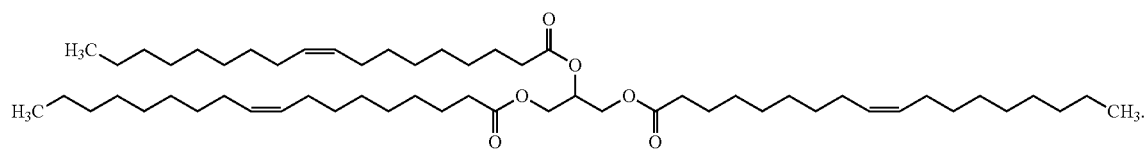

(II)

Embodiment 9 provides the lubricant of any one of Embodiments 4-8, wherein the second non-amphiphilic triglyceride has the structure according to Formula III:

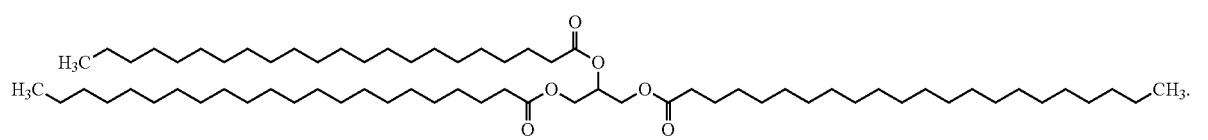

(III)

Embodiment 10 provides the lubricant of any one of Embodiments 1-9, wherein the first non-amphiphilic triglyceride and the second non-amphiphilic triglyceride independently are saturated, mono-unsaturated or poly-unsaturated.

Embodiment 11 provides the lubricant of any one of Embodiments 1-10, wherein the weight-average molecular weight of the first non-amphiphilic triglyceride is in a range of from about 500 g/mol to about 1000 g/mol.

Embodiment 12 provides the lubricant of any one of Embodiments 1-11, wherein the weight-average molecular weight of the first non-amphiphilic triglyceride is in a range of from about 800 g/mol to about 900 g/mol.

Embodiment 13 provides the lubricant of any one of Embodiments 1-12, wherein the weight-average molecular weight of the second non-amphiphilic triglyceride is in a range of from about 800 g/mol to about 1500 g/mol.

Embodiment 14 provides the lubricant of any one of Embodiments 1-13, wherein the weight-average molecular weight of the second non-amphiphilic triglyceride is in a range of from about 1000 g/mol to about 1200 g/mol.

Embodiment 15 provides the lubricant of any one of Embodiments 1-14, wherein a melting point of the first non-amphiphilic triglyceride and the second non-amphiphilic triglyceride is independently in a range of from about 3° C. to about 80° C.

Embodiment 16 provides the lubricant of any one of Embodiments 1-15, wherein a melting point of the first non-amphiphilic triglyceride and the second non-amphiphilic triglyceride are independently in a range of from about 5° C. to about 60° C.

Embodiment 17 provides the lubricant of any one of Embodiments 1-16, wherein a difference between a melting point of the first non-amphiphilic triglyceride and the melting point of the second non-amphiphilic triglyceride is in a range of from about 10° C. to about 70° C.

Embodiment 18 provides the lubricant of any one of Embodiments 1-17, wherein a melting point of the second non-amphiphilic triglyceride is greater than about 37° C.

Embodiment 19 provides the lubricant of any one of Embodiments 1-18, wherein the first non-amphiphilic triglyceride is in a range of from about 50 wt % to about 95 wt % of the lubricant.

Embodiment 20 provides the lubricant of any one of Embodiments 1-19, wherein the first non-amphiphilic triglyceride is in a range of from about 80 wt % to about 90 wt % of the lubricant.

Embodiment 21 provides the lubricant of any one of Embodiments 1-20, wherein the second non-amphiphilic triglyceride is in a range of from about 0.5 wt % to about 20 wt % of the lubricant.

Embodiment 22 provides the lubricant of any one of Embodiments 1-21, wherein the second non-amphiphilic triglyceride is in a range of from about 5 wt % to about 15 wt % of the lubricant.

Embodiment 23 provides the lubricant of any one of Embodiments 1-22, wherein the non-amphiphilic glycol ester is a polyglycol ester.

Embodiment 24 provides the lubricant of any one of Embodiments 1-23, wherein the non-amphiphilic glycol ester has a symmetric structure.

Embodiment 25 provides the lubricant of any one of Embodiments 1-24, wherein the non-amphiphilic glycol ester has the structure according to Formula IV:

$$R^4 \diagup O \diagup \diagup O \diagup \diagup O, \quad (IV)$$
$$\qquad \qquad \qquad O \diagup \diagup O$$
$$\qquad \qquad \qquad R^5$$

wherein $R^4$ and $R^5$ are independently chosen from substituted or unsubstituted ($C_2$-$C_{60}$)hydrocarbyl or a salt thereof.

Embodiment 26 provides the lubricant of Embodiment 25, wherein $R^4$ and $R^5$ are independently chosen from substituted or unsubstituted ($C_2$-$C_{60}$)alkyl, ($C_2$-$C_{60}$)alkenyl, ($C_2$-$C_{60}$)alkynyl, or a salt thereof.

Embodiment 27 provides the lubricant of Embodiment 25 or 26, wherein $R^4$ and $R^5$ are independently chosen from substituted or unsubstituted ($C_8$-$C_{30}$)alkyl, ($C_8$-$C_{30}$)alkenyl, or ($C_8$-$C_{30}$)alkynyl.

Embodiment 28 provides the lubricant of any one of Embodiments 25-27, wherein $R^4$ and $R^5$ are independently chosen from substituted or unsubstituted ($C_{14}$-$C_{20}$)alkyl or ($C_{14}$-$C_{20}$).

Embodiment 29 provides the lubricant of any one of Embodiments 25-28, wherein the non-amphiphilic glycol ester has the structure according to Formula V:

$$H_3C\text{~~~~~~~~~~~~~~~~}C(=O)O\text{~~}OC(=O)\text{~~~~~~~~~~~~~~~~}CH_3. \quad (V)$$

Embodiment 30 provides the lubricant of any one of Embodiments 1-29, wherein the non-amphiphilic glycol ester is in a range of from about 2 wt % to about 15 wt % of the lubricant.

Embodiment 31 provides the lubricant of any one of Embodiments 1-30, wherein the non-amphiphilic glycol ester is in a range of from about 3 wt % to about 6 wt % of the lubricant.

Embodiment 32 provides the lubricant of any one of Embodiments 1-31, wherein a viscosity of the lubricant is in a range of from about 5,000 cP to about 15,000 cP.

Embodiment 33 provides the lubricant of any one of Embodiments 1-32, wherein a viscosity of the lubricant is in a range of from about 8,000 cP to about 12,000 cP.

Embodiment 34 provides the lubricant of any one of Embodiments 1-33, wherein a flash point of the lubricant is at least 140 OC.

Embodiment 35 provides the lubricant of any one of Embodiments 1-34, wherein a flash point of the lubricant is at least 176° C.

Embodiment 36 provides the lubricant of any one of Embodiments 1-35, wherein the flash point of the lubricant is in a range of from about 140° C. to about 500° C.

Embodiment 37 provides the lubricant of any one of Embodiments 1-36, wherein the flash point of the lubricant is in a range of from about 150° C. to about 200° C.

Embodiment 38 provides the lubricant of any one of Embodiments 1-37, wherein the lubricant is substantially visually transparent when heated.

Embodiment 39 provides the lubricant of any one of Embodiments 1-38, further comprising a non-amphiphilic anti-inflammatory component.

Embodiment 40 provides the lubricant of any one of Embodiments 1-39, wherein the lubricant is a substantially homogenous composition.

Embodiment 41 provides the lubricant of any one of Embodiments 1-40, further comprising a non-amphiphilic fragrance compound.

Embodiment 42 provides the lubricant of any one of Embodiments 1-41, further comprising a non-amphiphilic anti-oxidant.

Embodiment 43 provides the lubricant of any one of Embodiments 1-42, wherein the lubricant is substantially free of amphiphilic compounds.

Embodiment 44 provides the lubricant of any one of Embodiments 1-43, wherein one or more amphiphilic compounds are less than about 0.01 wt % of the lubricant.

Embodiment 45 provides the lubricant of any one of Embodiments 1-44, wherein the first non-amphiphilic triglyceride has the structure according to Formula II:

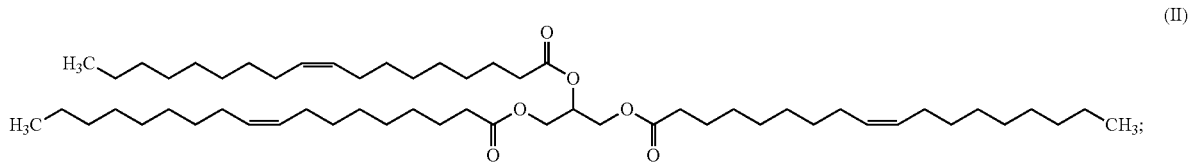 [SMILES: CCCCCCCC/C=C\CCCCCCCC(=O)OCC(COC(=O)CCCCCCC/C=C\CCCCCCCC)OC(=O)CCCCCCC/C=C\CCCCCCCC]

(II)

the second non-amphiphilic triglyceride has the structure according to Formula III:

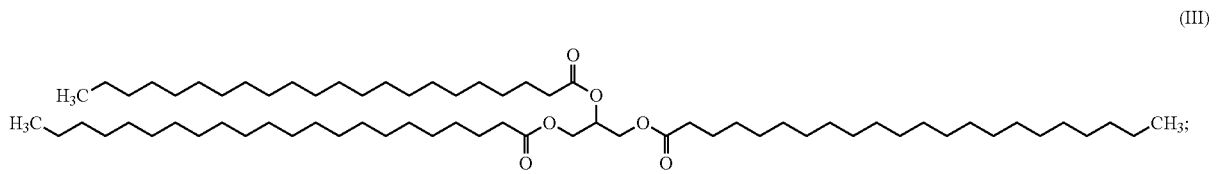 [SMILES: CCCCCCCCCCCCCCCCCCCCCC(=O)OCC(COC(=O)CCCCCCCCCCCCCCCCCCCCC)OC(=O)CCCCCCCCCCCCCCCCCCCCC]

(III)

and
the non-amphiphilic glycol ester has the structure according to Formula V:

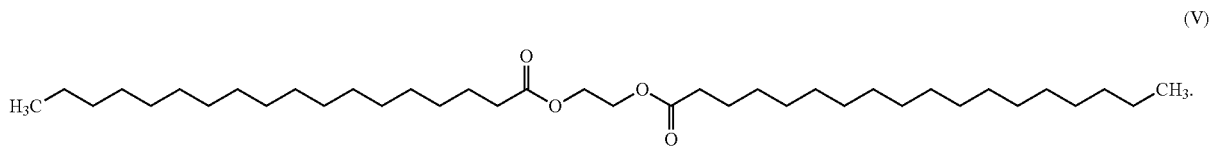 [SMILES: CCCCCCCCCCCCCCCCCC(=O)OCCOC(=O)CCCCCCCCCCCCCCCCC]

(V)

Embodiment 46 provides a method of making the lubricant of any one of Embodiments 1-45, the method comprising contacting the first non-amphiphilic triglyceride, the second non-amphiphilic triglyceride, and the non-amphiphilic glycol ester.

Embodiment 47 provides the method of Embodiment 46, further comprising heating.

Embodiment 48 provides the method of Embodiment 47, wherein the first non-amphiphilic triglyceride is heated to a temperature in a range of from about 70° C. to about 100° C.

Embodiment 49 provides the method of any one of Embodiments 47 or 48, wherein the first non-amphiphilic triglyceride is heated to a temperature in a range of from about 80° C. to about 95° C.

Embodiment 50 provides the method of any one of Embodiments 46-49, wherein contacting comprises stirring.

Embodiment 51 provides the method of Embodiment 50, wherein stirring is at about 40 rpm to about 150 rpm.

Embodiment 52 provides the method of any one of Embodiments 50 or 51, wherein stirring is at about 60 rpm to about 120 rpm.

Embodiment 53 provides a kit comprising:
a container; and
the lubricant of any one of Embodiments 1-52.
Embodiment 54 provides a probe comprising:
a tip; and
the lubricant of any one of Embodiments 1-53 in contact with at least a portion of the tip.

Embodiment 55 provides the probe of Embodiment 54, wherein the tip comprises a metal, a ceramic, a composite, a plastic or a mixture thereof.

Embodiment 56 provides the probe of Embodiment 55, wherein metal comprises a stainless steel.

Embodiment 57 provides the probe of any one of Embodiments 55 or 56, wherein the metal is chosen from SAE 304 stainless steel, SAE 316 stainless steel, and a mixture thereof.

Embodiment 58 provides the probe of any one of Embodiments 55-57, further comprising a polymerized product of the first and second non-amphiphilic triglycerides coating at least a portion of the tip.

Embodiment 59 provides the probe of any one of Embodiments 55-58, wherein the probe is an electro-cautery probe, a scalpel, a heated scalpel, an ultrasonic cutting device, or a radio frequency probe.

Embodiment 60 provides a method of coating a cautery probe, the method comprising:
contacting a tip of the probe with the lubricant of any one of Embodiments 1-59.

Embodiment 61 provides a method of cauterization comprising cauterizing tissue with the probe comprising a tip, the tip comprising the lubricant of any one of Embodiments 1-60.

Embodiment 62 provides the method of Embodiment 61, comprising performing cauterizing of the tissue with a robot.

The invention claimed is:

1. A lubricant comprising:
   a first non-amphiphilic triglyceride, in a range of from about 55 wt % to about 95 wt % of the lubricant;
   a second non-amphiphilic triglyceride in a range of from about 7 wt % to about 20 wt %, the second non-amphiphilic triglyceride being different from the first non-amphiphilic triglyceride, wherein the second non-amphiphilic triglyceride has the structure according to Formula III:

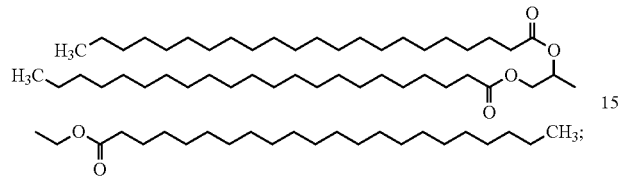
(III)

and
   a non-amphiphilic glycol ester.

2. The lubricant of claim 1, wherein the first non-amphiphilic triglyceride and the second non-amphiphilic triglyceride independently have a structure according to Formula

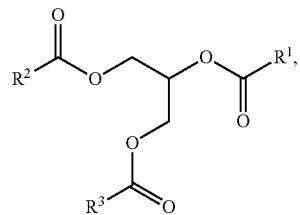
(I)

wherein $R^1$, $R^2$, and $R^3$ are independently chosen from substituted or unsubstituted $C_2$-$C_{60}$)hydrocarbyl and a salt thereof.

3. The lubricant of claim 2, wherein $R^1$, $R^2$, and $R^3$ are independently chosen from substituted or unsubstituted ($C_2$-$C_{60}$)alkyl, ($C_2$-$C_{60}$)alkenyl, ($C_2$-$C_{60}$)alkynyl, ($C_2$-$C_{60}$)acyl, or a mixture thereof.

4. The lubricant of claim 2, wherein the first non-amphiphilic triglyceride has the structure according to Formula

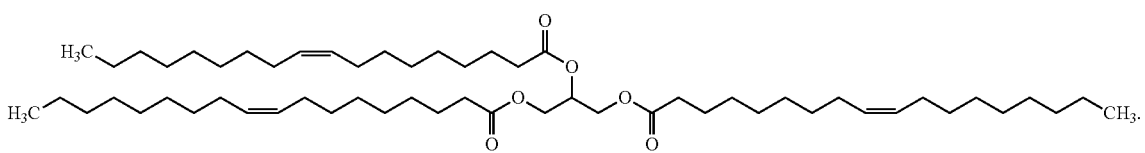
(II)

5. The lubricant of claim 1, wherein a melting point of the second non-amphiphilic triglyceride is greater than about 37° C.

6. The lubricant of claim 1, wherein the second non-amphiphilic triglyceride is in a range of from about 10 wt % to about 20 wt % of the lubricant.

7. The lubricant of claim 1, wherein the non-amphiphilic glycol ester has the structure according to Formula IV:

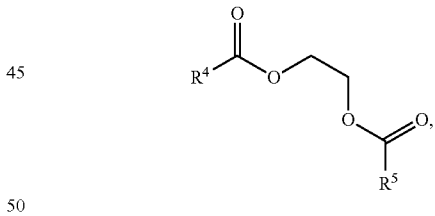
(IV)

wherein $R^4$ and $R^5$ are independently chosen from substituted or unsubstituted $C_2$-$C_{60}$) hydrocarbyl or a salt thereof.

8. The lubricant of claim 7, wherein $R^4$ and $R^5$ are independently chosen from substituted or unsubstituted ($C_2$-$C_{60}$)alkyl, ($C_2$-$C_{60}$)alkenyl, ($C_2$-$C_{60}$)alkynyl, or a salt thereof.

9. The lubricant of claim 7, wherein the non-amphiphilic glycol ester has the structure according to Formula V:

(V)

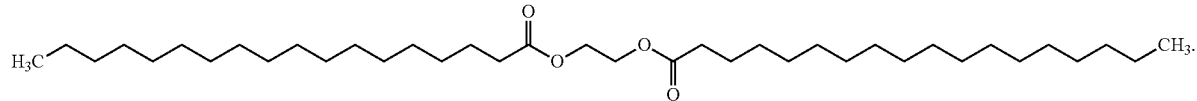

10. The lubricant of any one of claim 1, wherein the non-amphiphilic glycol ester is in a range of from about 2 wt % to about 15 wt % of the lubricant.

11. The lubricant of claim 1, wherein the flash point of the lubricant is in a range of from about 140° C. to about 500° C.

12. The lubricant of claim 1, wherein the lubricant is substantially visually transparent when heated.

13. The lubricant of claim 1, wherein one or more amphiphilic compounds are less than about 0.01 wt % of the lubricant.

14. The lubricant of claim 1, wherein
the first non-amphiphilic triglyceride has the structure according to Formula II:

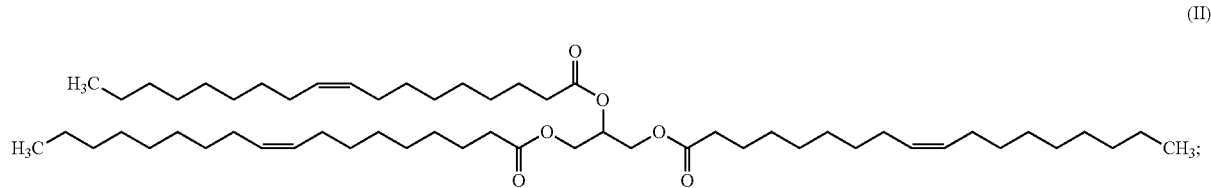 [SMILES: CCCCCCCC/C=C\CCCCCCCC(=O)OCC(COC(=O)CCCCCCC/C=C\CCCCCCCC)OC(=O)CCCCCCC/C=C\CCCCCCCC]

(II)

the second non-amphiphilic triglyceride has the structure according to Formula III:

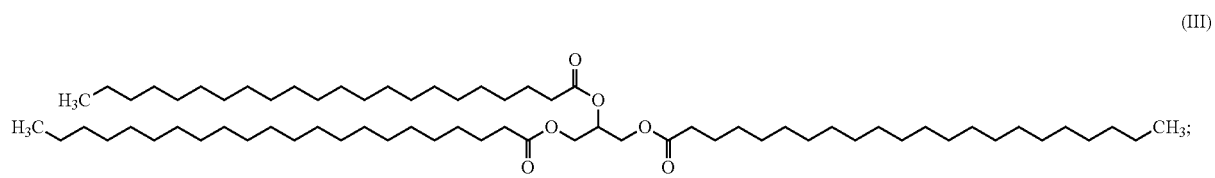 [SMILES: CCCCCCCCCCCCCCCCCCCCCC(=O)OCC(COC(=O)CCCCCCCCCCCCCCCCCCCCC)OC(=O)CCCCCCCCCCCCCCCCCCCCC]

(III)

and
the non-amphiphilic glycol ester has the structure according to Formula V:

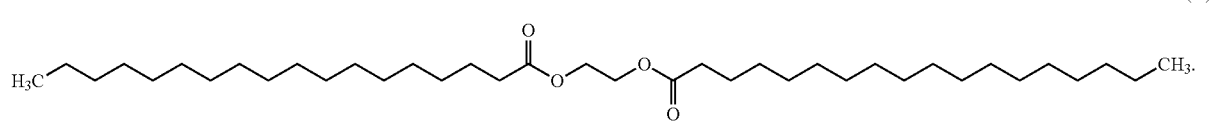

(V)

15. A method of making the lubricant of claim 1, the method comprising contacting a first non-amphiphilic triglyceride, a second non-amphiphilic triglyceride, and a non-amphiphilic glycol ester, wherein the first non-amphiphilic triglyceride is present in a range of from about 55 wt % to about 95 wt % of the lubricant and the second non-amphiphilic triglyceride in a range of from about 7 wt % to about 20 wt %.

16. A probe comprising:
a tip; and
a lubricant in contact with at least a portion of the tip, the lubricant comprising:
a first non-amphiphilic triglyceride, in a range of from about 55 wt % to about 95 wt % of the lubricant;
a second non-amphiphilic triglyceride in a range of from about 7 wt % to about 20 wt %, different from the first non-amphiphilic triglyceride, wherein the second non-amphiphilic triglyceride has the structure according to Formula III:

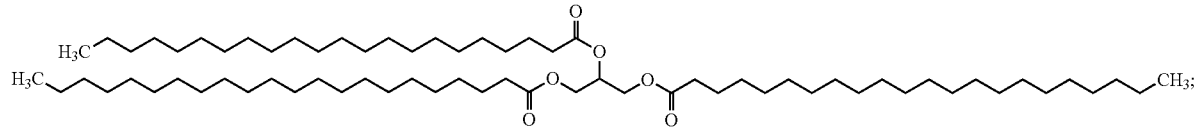

(III)

and
a non-amphiphilic glycol ester.

17. The probe of claim 16, further comprising a polymerized product of the first and second non-amphiphilic triglycerides coating at least a portion of the tip.

18. The probe of claim 16, wherein the probe is an electro-cautery probe, a scalpel, a heated scalpel, an ultrasonic cutting device, or a radio frequency probe.

19. The lubricant of claim 14, wherein:
the first non-amphiphilic triglyceride, in a range of from about 83 wt % to about 90 wt % of the lubricant;
the second non-amphiphilic triglyceride, different from the first non-amphiphilic triglyceride, in a range of from about 10 wt % to about 15 wt % of the lubricant; and
the non-amphiphilic glycol ester, in a range of from about 3 wt % to about 6 wt % of the lubricant.

\* \* \* \* \*